(12) United States Patent
Craig et al.

(10) Patent No.: US 7,476,253 B1
(45) Date of Patent: Jan. 13, 2009

(54) HUMERAL HEAD PRESERVING IMPLANT

(75) Inventors: Edward V Craig, New Canaan, CT (US); Russell Warren, Greenwich, CT (US); Nathan A Winslow, Warsaw, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 745 days.

(21) Appl. No.: 10/916,102

(22) Filed: Aug. 11, 2004

(51) Int. Cl.
*A61F 2/40* (2006.01)
(52) U.S. Cl. .................................... 623/19.14
(58) Field of Classification Search ................ 623/22.4, 623/22.43, 23.26, 19.11, 19.12, 19.13, 19.14
See application file for complete search history.

(56) References Cited

U.S. PATENT DOCUMENTS

| | | | | |
|---|---|---|---|---|
| 4,865,605 A * | 9/1989 | Dines et al. | ............... | 623/19.14 |
| 5,507,817 A | 4/1996 | Craig et al. | | |
| 5,580,352 A * | 12/1996 | Sekel | ...................... | 623/22.46 |
| 5,702,486 A | 12/1997 | Craig et al. | | |
| 5,772,662 A * | 6/1998 | Chapman et al. | .............. | 606/69 |
| 5,849,004 A * | 12/1998 | Bramlet | ...................... | 606/232 |
| 5,928,235 A * | 7/1999 | Friedl | ........................... | 606/64 |
| 5,984,927 A * | 11/1999 | Wenstrom et al. | ............. | 606/72 |
| 5,984,966 A * | 11/1999 | Kiema et al. | ............. | 623/13.14 |
| 6,183,474 B1 * | 2/2001 | Bramlet et al. | ................ | 606/66 |
| 6,443,954 B1 * | 9/2002 | Bramlet et al. | ................ | 606/62 |
| 6,511,481 B2 | 1/2003 | von Hoffmann et al. | | |
| 6,562,042 B2 | 5/2003 | Nelson | | |
| 6,648,890 B2 * | 11/2003 | Culbert et al. | ................ | 606/63 |
| 7,118,572 B2 * | 10/2006 | Bramlet et al. | ................ | 606/66 |
| 7,273,499 B2 * | 9/2007 | McCleary et al. | ........ | 623/18.11 |
| 2003/0074080 A1 * | 4/2003 | Murray | ..................... | 623/22.42 |
| 2004/0010257 A1 * | 1/2004 | Cachia et al. | ................. | 606/72 |

FOREIGN PATENT DOCUMENTS

GB 2033755 A * 5/1980

* cited by examiner

*Primary Examiner*—Thomas J Sweet
(74) *Attorney, Agent, or Firm*—Harness, Dickey & Pierce, P.L.C.

(57) ABSTRACT

A modular humeral implant and associated kit and method for implantation into a humerus that includes a natural humeral shaft and a natural humeral head. The modular implant includes a humeral stem for implantation into the natural humeral shaft, and an adapter. The adapter includes an anchoring projection and is operable for coupling to the humeral stem. The anchoring projection is adapted for insertion into an underside of the natural humeral head.

24 Claims, 11 Drawing Sheets

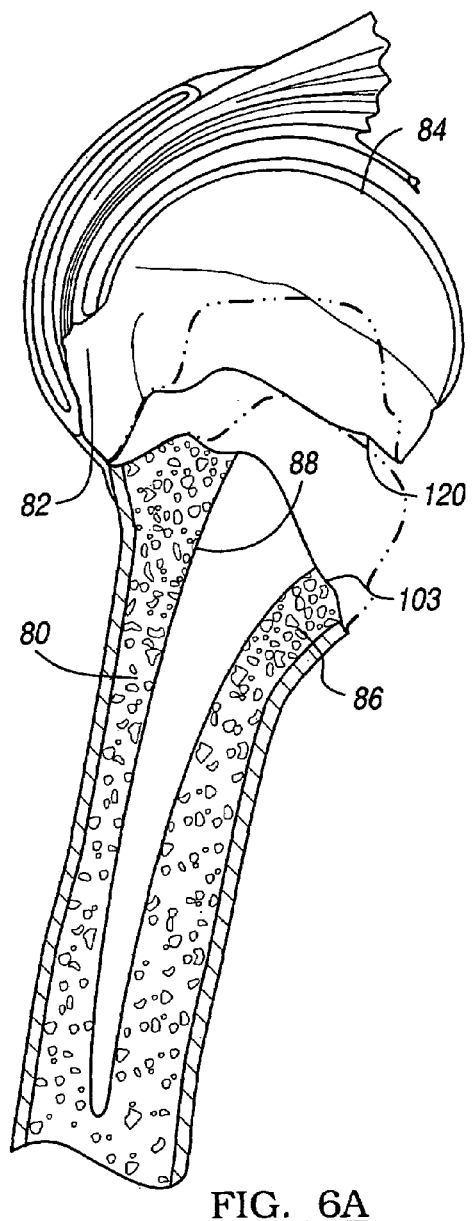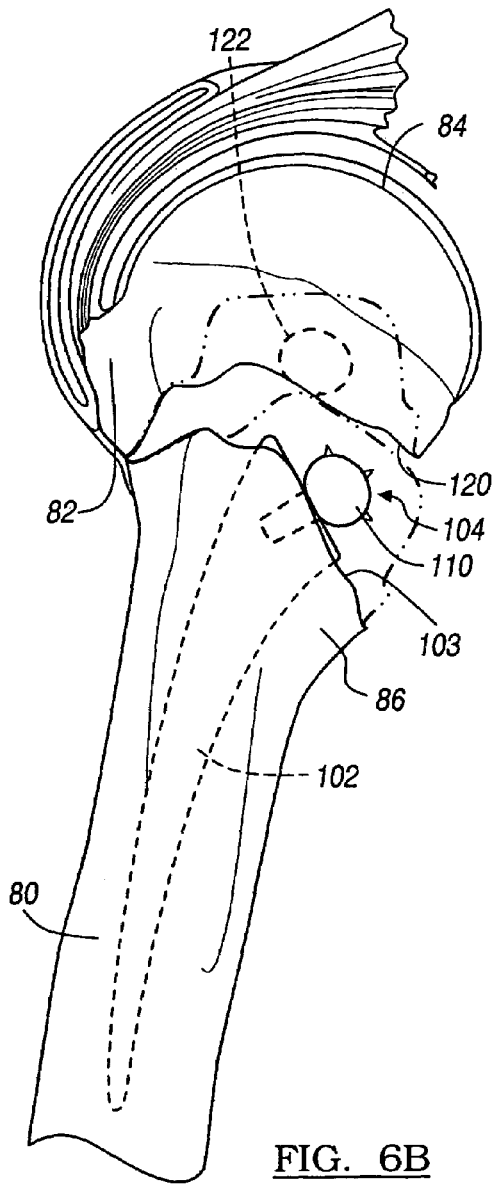
FIG. 6A
FIG. 6B

HUMERAL HEAD PRESERVING IMPLANT

INTRODUCTION

A humeral prosthesis for total shoulder joint replacement generally includes a prosthetic humeral stem and a prosthetic humeral head which replaces the natural humeral head and is disposed within the shoulder socket. For three and four-part humeral head split fractures in which the blood supply to the fragments is compromised, a hemiarthroplasty can be performed, also replacing the humeral head with a prosthetic head.

In some humeral fractures, however, blood supply to the head fragment may be adequate, such as, for example, when the head is still attached to one of the tuberosities. In such cases, repairing and salvaging the natural head is preferable to replacing it. Accordingly, prostheses that allow retention and/or repair of the natural humeral head are still desirable.

SUMMARY

Various aspects of the invention teach a modular humeral implant and associated kit and method for implantation into a humerus that includes a natural humeral shaft and a natural humeral head. The modular implant includes a humeral stem for implantation into the natural humeral shaft, and an adapter. The adapter includes an anchoring projection and is operable for coupling to the humeral stem. The anchoring projection is adapted for insertion into an underside of the natural humeral head.

The present teachings also provide a method for implanting a modular humeral prosthesis to repair a humeral fracture in which the natural humeral head is still attached to a portion of the natural humeral shaft. The method includes rotating the natural humeral head to expose the proximal surface of the natural humeral shaft without severing the attachment. A longitudinal bore is prepared into the humeral shaft. An adapter is coupled to one of the natural humeral head and a humeral stem, and the humeral stem is implanted into the longitudinal bore. The natural humeral head is rotated onto the natural humeral shaft such that the adapter is inserted into the other of the natural humeral head and the humeral stem, and the natural humeral head substantially contacts the natural humeral shaft.

The present teachings also provide a modular humeral implant for implantation into a humerus that includes a natural humeral shaft and a natural humeral head. The implant includes a humeral stem for implantation into the natural humeral shaft, and a plurality of fasteners fastening the natural humeral shaft through the humeral stem to the natural humeral head.

The present teachings also provide a method for implanting a modular humeral prosthesis to repair a humeral fracture in which the natural humeral head is still attached to a portion of the natural humeral shaft. The method includes rotating the natural humeral head to expose a proximal surface of the natural humeral shaft without severing the attachment, preparing a longitudinal bore into the natural humeral shaft; inserting the humeral stem into the bore, rotating the natural humeral head onto the proximal surface of the natural humeral shaft, drilling a plurality of angled bores extending from natural humeral shaft though the humeral stem to the natural humeral head, and inserting fasteners through the angled bores to attach the natural humeral shaft to the natural humeral head.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 6A-6C illustrate a sequence of implantation procedures according to the present teachings.

DETAILED DESCRIPTION

Figures 1, 1G:
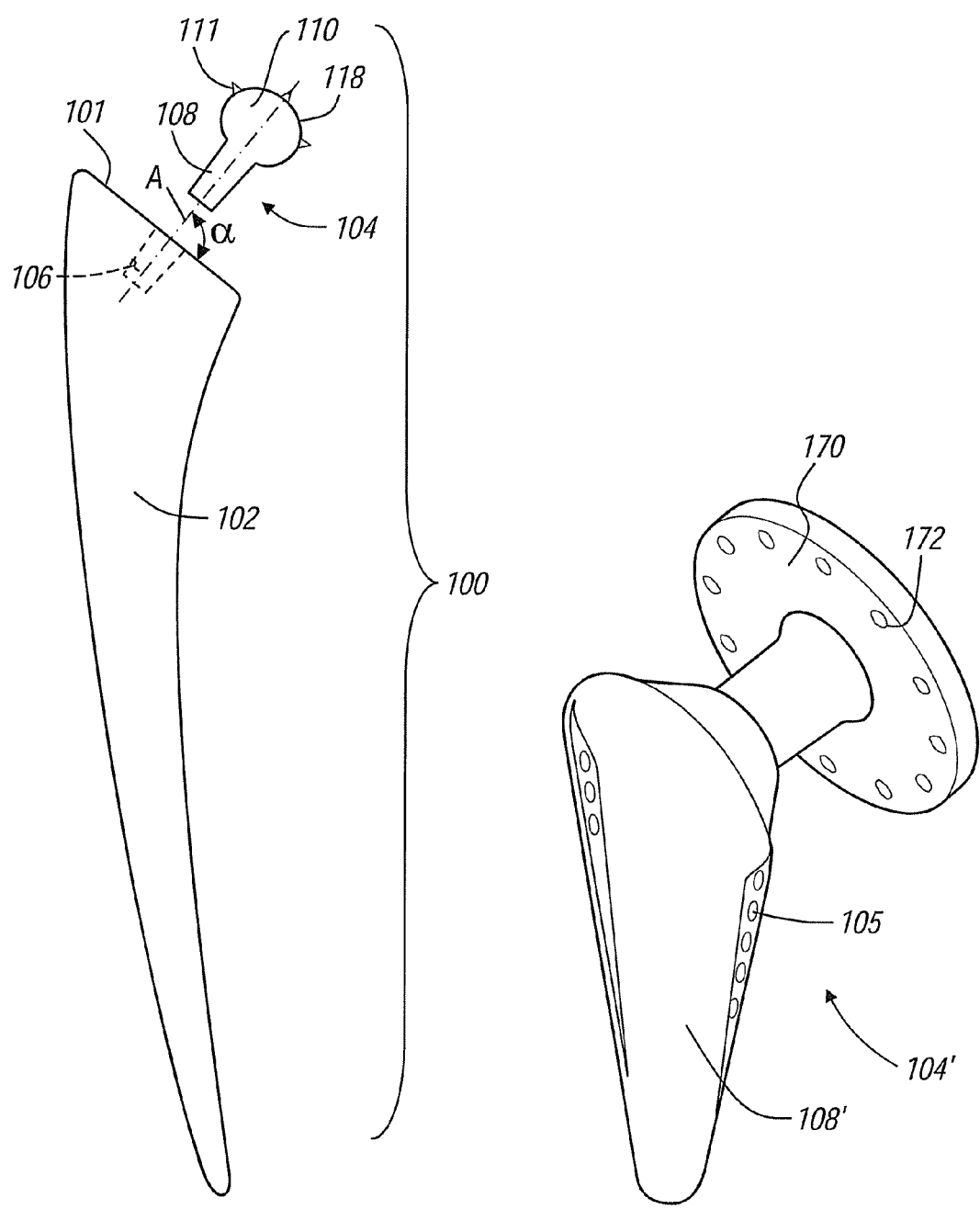
FIG. 1 is an exploded view of a humeral implant according to the present teachings.
FIG. 1G is isometric view of a humeral implant according to the present teachings.

The following description of various embodiments is merely exemplary in nature and is in no way intended to limit the invention, its application, or uses.

Referring to FIGS. 1-4, a modular humeral implant 100 includes a humeral stem 102 and an adapter 104. The humeral stem 102 is adapted to be inserted into a natural humeral shaft 80, which can be prepared to receive the humeral stem 102 using methods known in the art, such as reaming, drilling, etc. The humeral stem 102 can be integral or modular, including two or more separate components, and can be provided in variable lengths and shapes. The adapter 104 functions to connect, the implanted humeral stem 102 and the natural humeral head 84. The natural humeral head 84 can be intact or reconstructed from fracture fragments by methods known in the art. The natural humeral head 84 can be still attached to a portion of the natural humeral shaft 80, such as, for example, one of the tuberosities 82. Because the natural humeral head 84 remains attached to the tuberosity 82, blood supply to the natural humeral head 84 can be preserved, thus improving the therapeutic outcome relative to the risk of localized necrosis. The humeral implant 100 can be implanted without severing the attachment of the natural humeral head 84 to the tuberosity 82, as is discussed below.

Figure 1A:
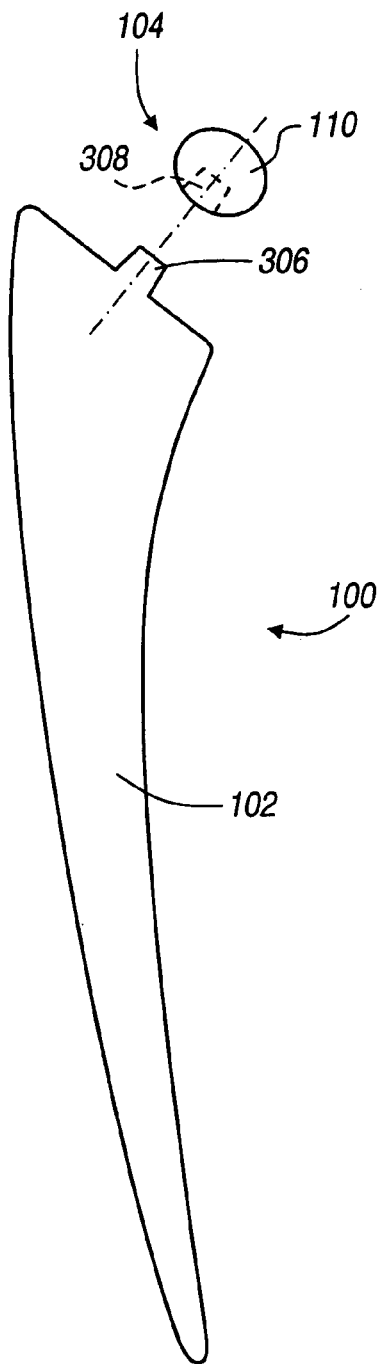
FIG. 1A is an exploded view of a humeral implant according to the present teachings.
Figure 1B:
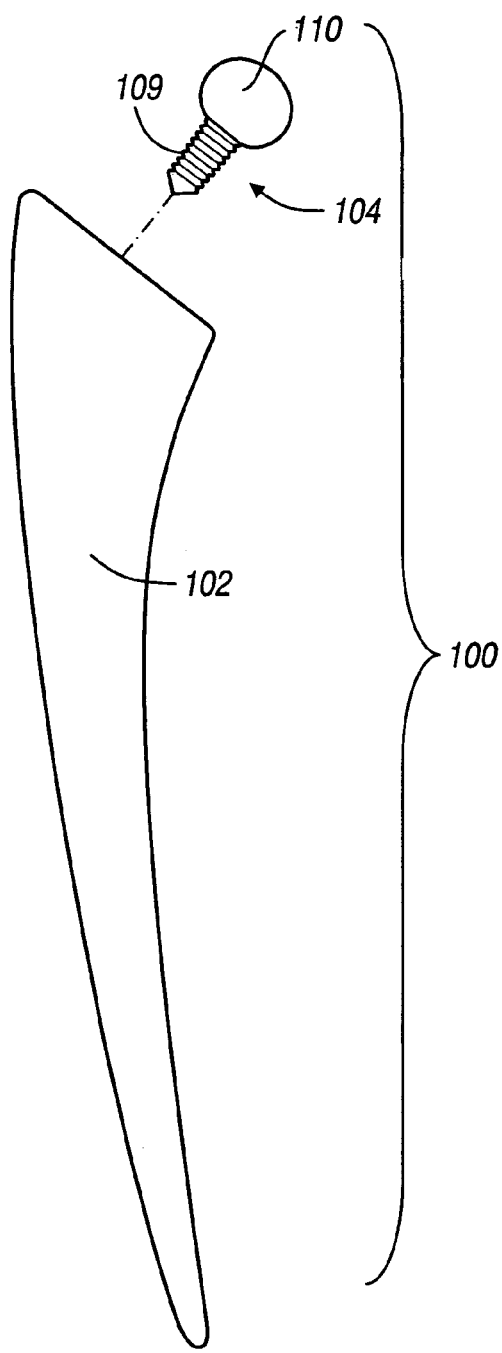
FIG. 1B is an exploded view of a humeral implant according to the present teachings.
Figure 2:
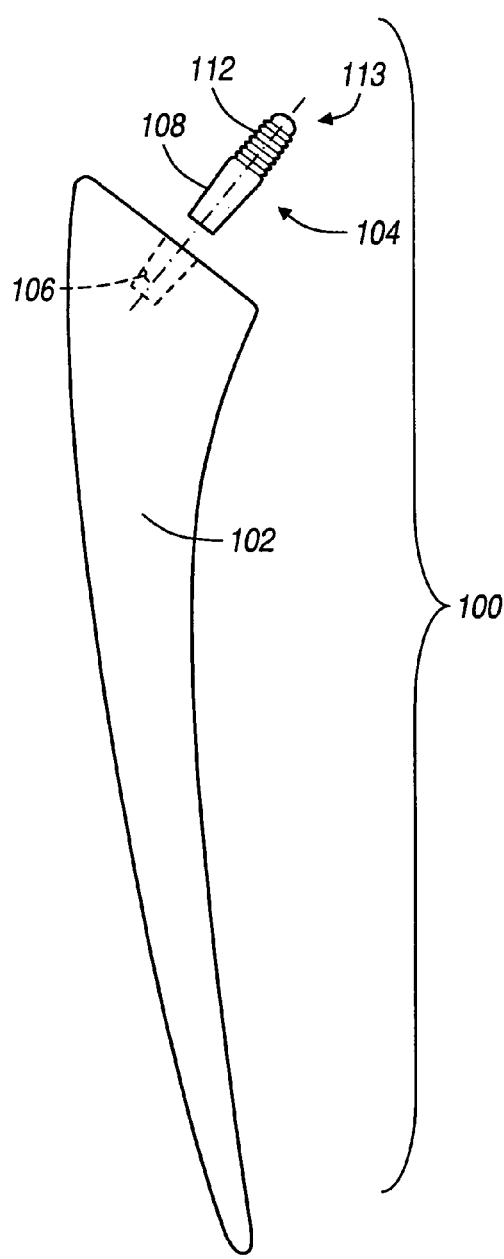
FIG. 2 is an exploded view of a humeral implant according to the present teachings.
Figure 3:
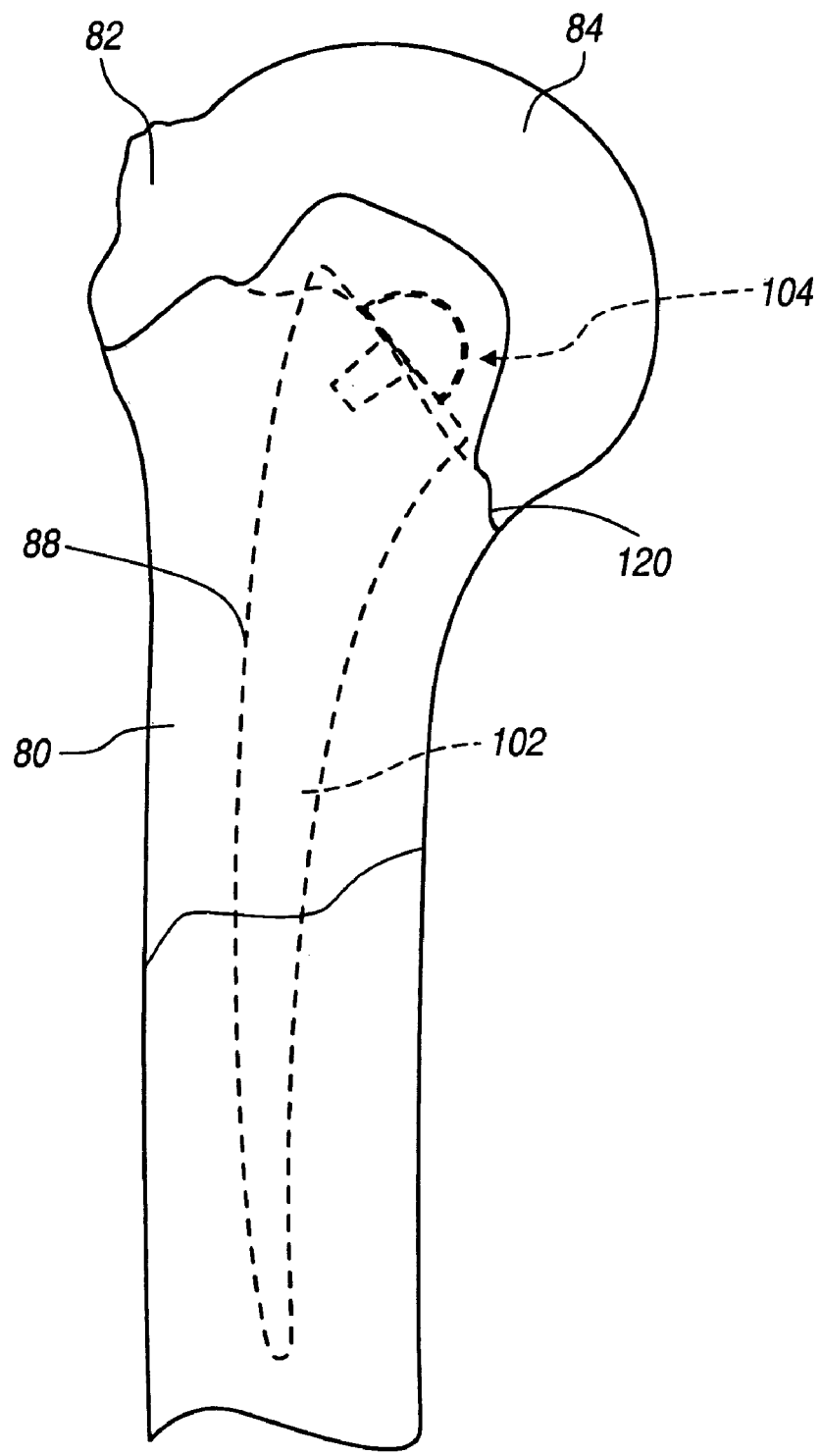
FIG. 3 is an environmental view of the humeral implant of FIG. 1.
Figure 4:
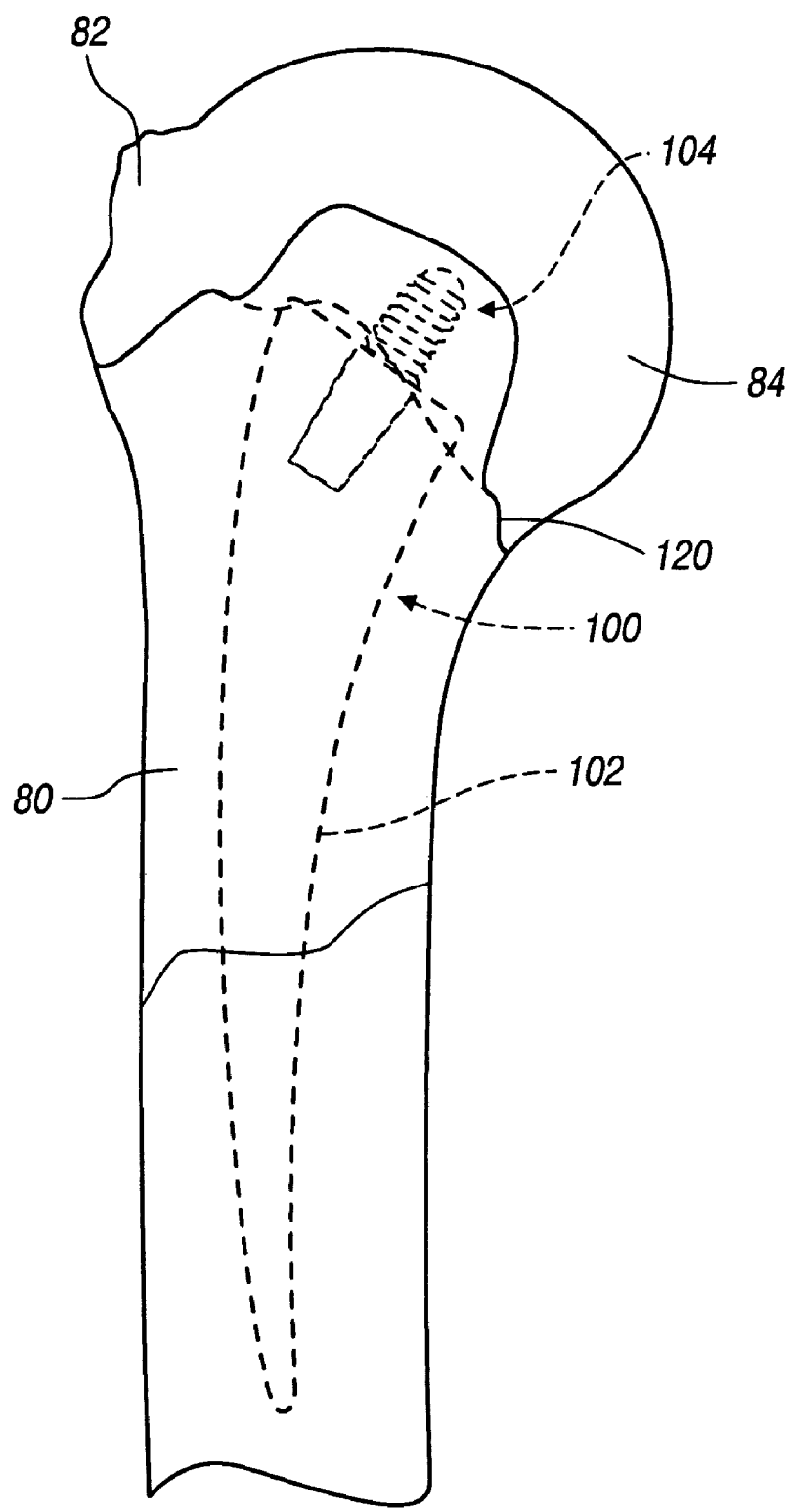
FIG. 4 is an environmental view of the humeral implant of FIG. 2.

Referring to FIG. 1, the humeral stem 102 can include a proximal tapered recess 106 that is adapted to taper lock with a tapered projection 108 of the adapter 104. Alternatively, as shown in FIG. 1A, the humeral stem 102 can include a tapered projection 306 that interlocks with a mating tapered recess 308 of the adaptor 104. The angle α between a longitudinal axis A of the adapter 104 and a proximal end surface 101 of the humeral stem 102 can be 90° or any other angle as desired under particular circumstances. The adapter 104 includes an anchoring projection 113 which is adapted for insertion into an underside surface 120 of the natural humeral head 84. The anchoring projection 113 can be a ribbed projection or threaded screw 112, as illustrated in FIGS. 2 and 4, or a bulbous projection 110 that defines a convex surface 118, as illustrated in FIGS. 1 and 3. The bulbous projection 110 can be a ball or a portion of a sphere or ellipsoid or a polyhedral three-dimensional shape, or any other suitable three-dimensional shape. The bulbous projection 110 can be bioabsorbable or metallic with an attachment device 111 that includes a porous-coating to promote bone ongrowth and ingrowth. The attachment device 111 of the bulbous projection 110 can also define barbs, spikes, threads, grooves or other devices. Instead of a taper-lock, the bulbous projection 110 can also be coupled to the humeral stem 102 using any other means, such as a threaded screw 109 that is threaded from the humeral stem 102 into the bulbous projection 110, as shown in FIG. 1B, or vice-versa.

The threaded screw 112 can be directly threaded into cancellous bone through the underside surface 120 of the natural humeral head 84. To receive the bulbous projection 110, the natural humeral head 84 can be prepared by removing, if necessary, cancellous bone from the underside surface 120 of the natural humeral head 84 to create a snugly-fitting recess 122. Alternatively, a cancellous bone impactor (not shown) can be used to define a recess 122 that snugly matches the bulbous projection 110.

Figure 3A:
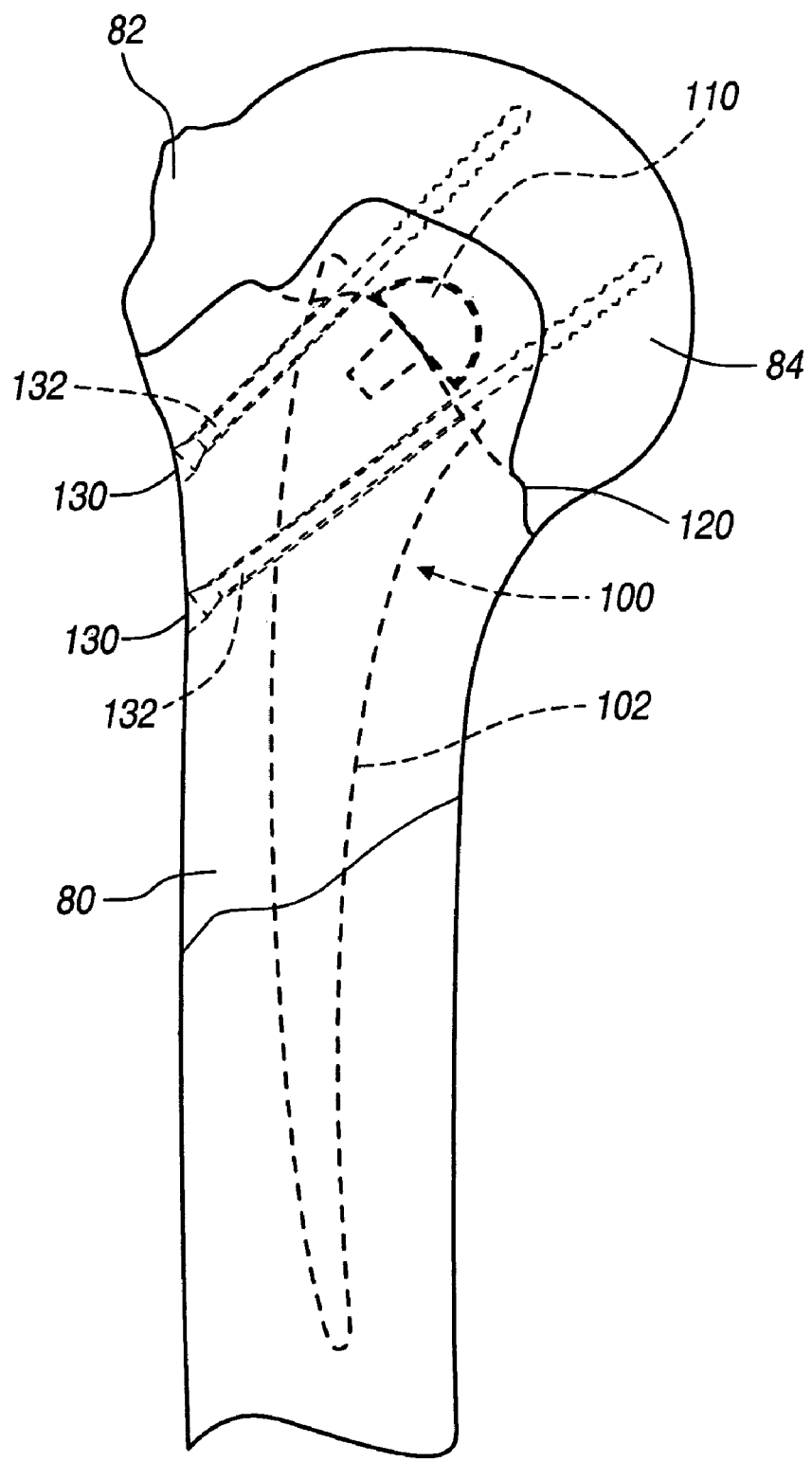
FIG. 3A is an environmental view of a humeral implant according to the present teachings.

Referring to FIG. 3A, one or more fasteners 132 inserted into corresponding angled bores 130 can be used to re-attach the natural humeral head 84 either exclusively or in conjunction with the projection 110. The fasteners 132 could be placed through the natural humeral shaft 80 and the humeral stem 102 after the humeral head 84 is impacted onto the projection 110 to provide initial stability to the natural humeral head 84. For proper placement, the angled bores 130 can be drilled through the natural humeral shaft 80 and/or tuberority 82 after the humeral stem 102 is inserted into the humeral canal. The fasteners 132 could be made of resorbable polylactide, polyglycolide, or combination thereof, or calcium phosphate, bone morphogenetic protein, allograft, etc., or any other biocompatible material.

Figure 1C:
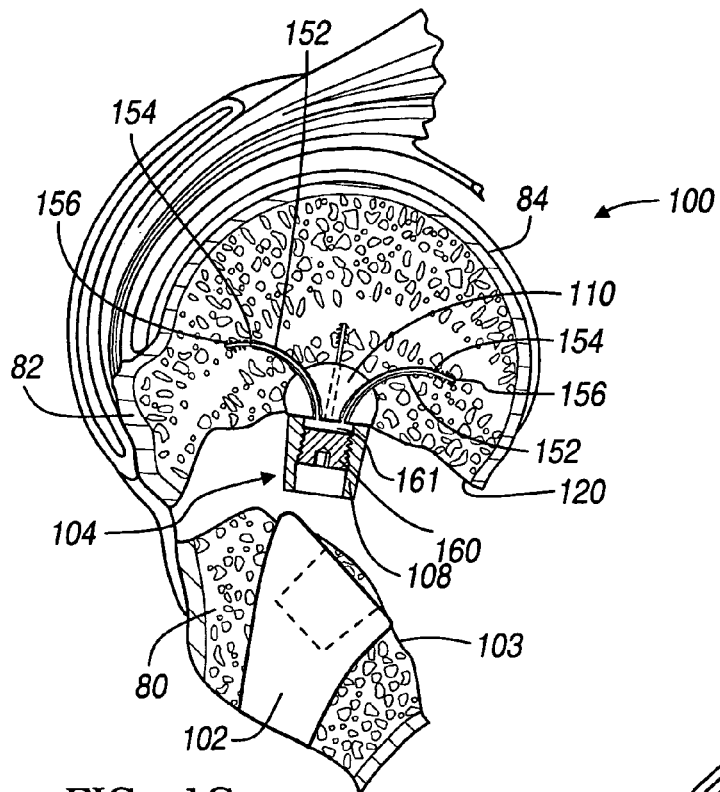
FIG. 1C is a partially assembled environmental view of a humeral implant according to the present teachings.

Referring to FIG. 1C, the bulbous projection 110 of the adaptor 104 can include guiding bores 152 through which anchoring wires 154 pass to be embedded in the natural humeral head 84. The anchoring wires 154 can be attached to a base plate 161 at the base of the bulbous projection 110, and are pushed into the natural humeral head 84 by a set screw or other fastener 160, which is inserted through the tapered projection 108 and pushes against the base plate 161. The anchoring wires 154 can be made of nitinol or other biocompatible material and can have barbs 156.

Figure 1E:
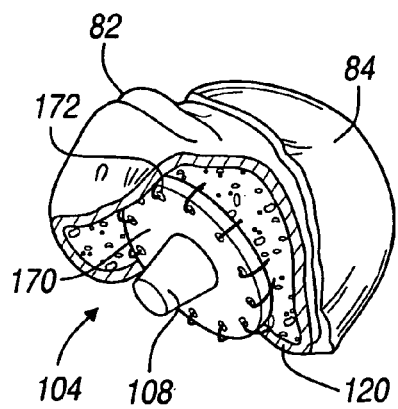
FIG. 1E is an isometric environmental view of the adapter of FIG. 1D.
Figure 1D:
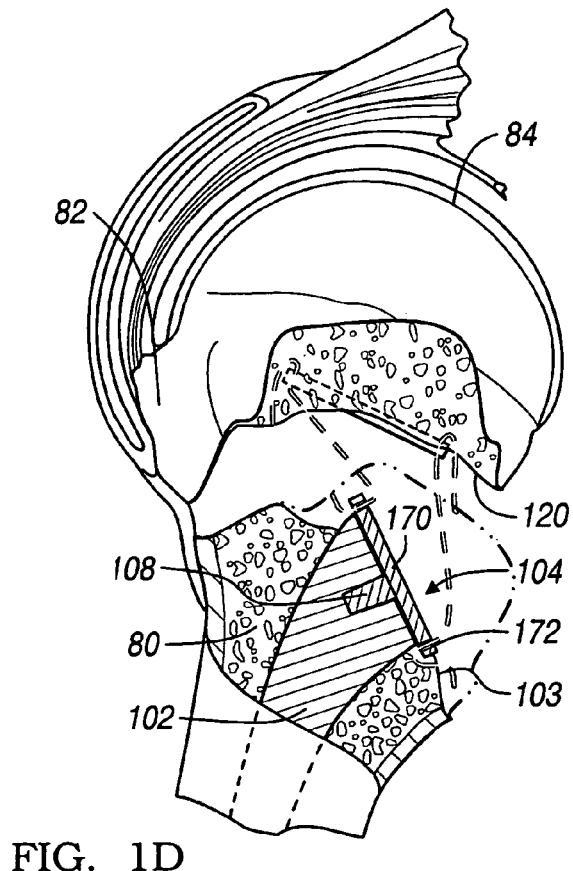
FIG. 1D is a partially assembled environmental view of a humeral implant according to the present teachings.
Figure 1F:
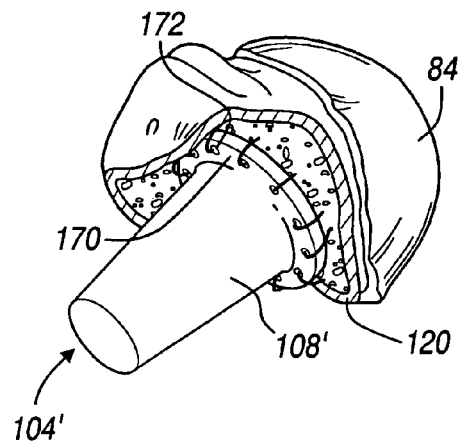
FIG. 1F is an environmental isometric view of a humeral implant according to the present teachings.

Referring to FIGS. 1D and 1E, the adapter 104 can include a disk-shaped projection 170, which can be integrally or modularly attached to the tapered projection 108. The disk-shaped projection 170 has peripheral suturing holes 172 to allow suturing to the natural humeral head 84. The disk-shaped projection 170 can be circular or polygonal or have any other flat shape and can be recessed into the natural humeral head 84, such that the disk-shaped projection 170 is flush with the underside surface 120 of the natural humeral head 84. In another aspect, illustrated in FIG. 1F, the adapter 104 can be replaced with an adapter-stem combination 104', such that the disk-shaped projection 170 is directly coupled to a humeral stem 108'. It will be appreciated that the humeral stem 108' can be selected from any suitable stems including a Copeland-style stem 108' illustrated in FIG. 1F, a short hip-style stem 108' illustrated in FIG. 1G, etc. The stem 108' can be porous coated and can include suturing holes 105.

Figure 2A:
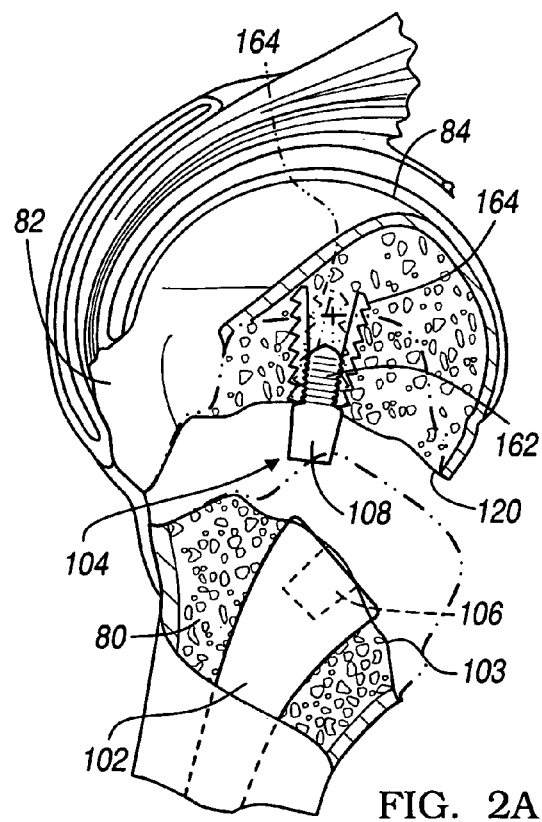
FIG. 2A is a partially assembled environmental view of a humeral implant according to the present teachings.
Figure 2B:
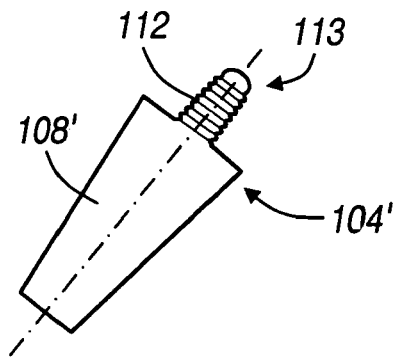
FIG. 2B is a side view of a humeral implant according to the present teachings.
Figure 2C:
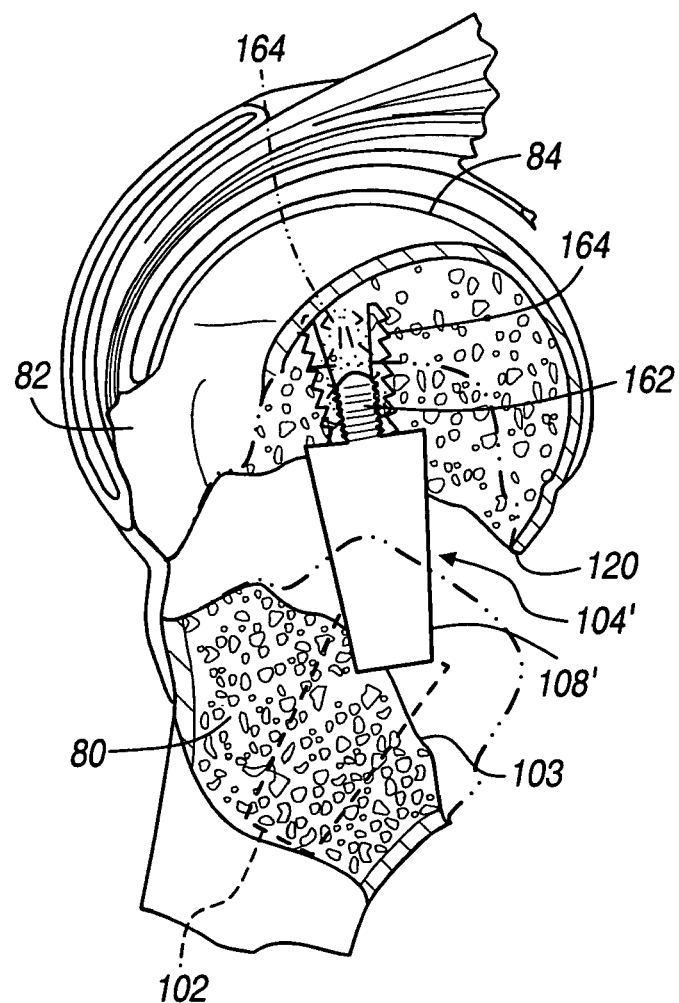
FIG. 2C is an environmental sectional view of a humeral implant according to the present teachings.

Referring to FIG. 2A, the adapter 104 can be modular and include a tapered projection 108 and an expandable tubular sleeve 164 that is received in the natural humeral head 84. A plug 162 extends from the tapered projection 108. The plug 162 is inserted into the sleeve 164 causing to expand and lock into the natural humeral head 84. In another aspect, illustrated in FIG. 2C, the adapter 104 is replaced with an adapter-stem combination 104', such that the plug 162 is directly coupled to a humeral stem 108', such as a short hip stem. In yet another aspect illustrated in FIG. 2B, the anchoring projection 113 is also directly coupled to a humeral stem 108', such as a short hip stem.

Figure 5:
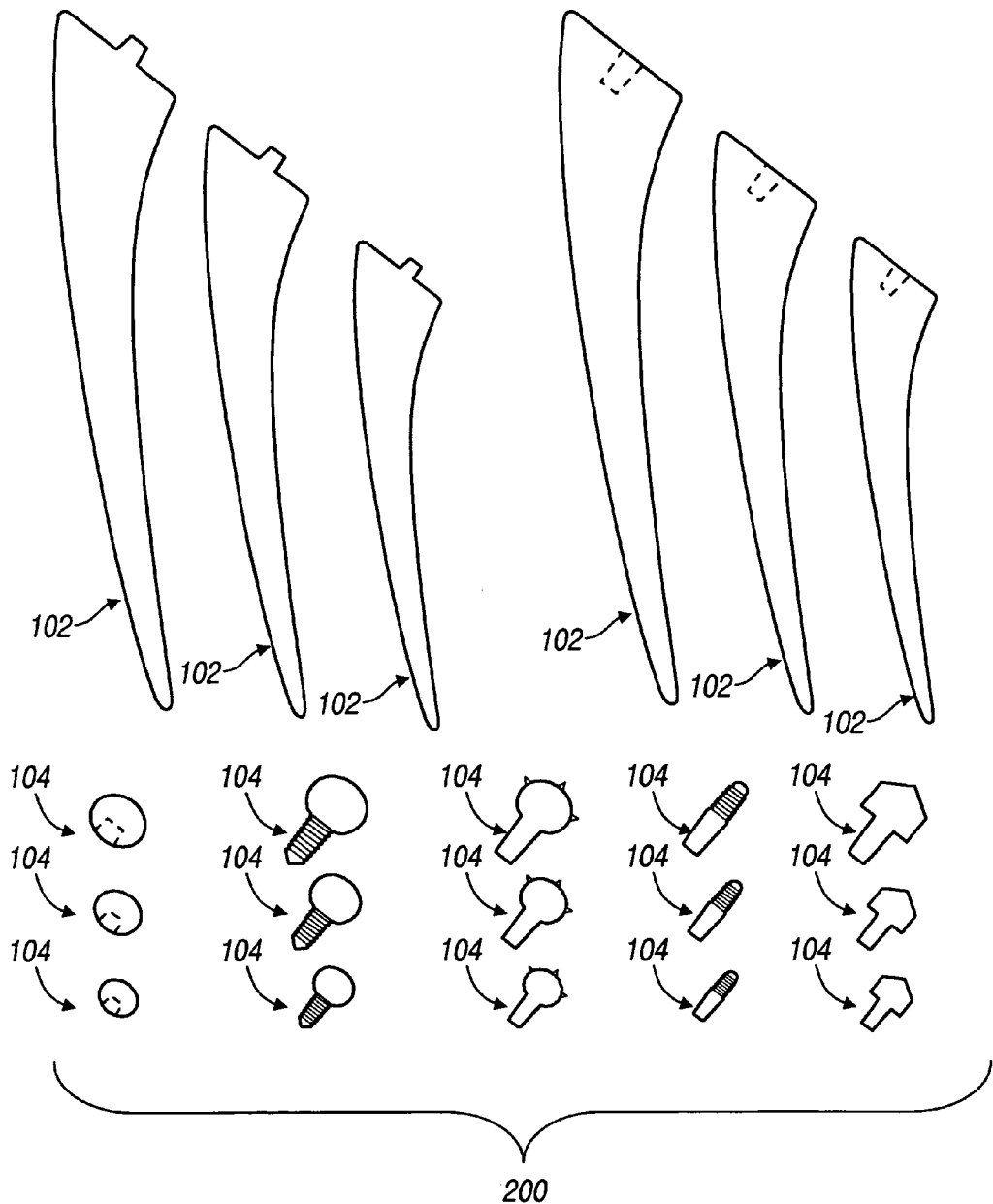
FIG. 5 is kit of modular humeral components according to the present teachings.

Referring to FIG. 5, separate adapters 104 having differently shaped and sized anchoring projections 113, and humeral stems 102 of different shapes and sizes can be assembled together as a kit 200 and made available to the operating surgeon for optimal intraoperative selection depending on the particular patient and condition encountered during reconstructive surgery. Various size fasteners 132 (shown in FIG. 3A) can also be included in the kit. Although not specifically shown in FIG. 5, the kit 200 can also include adapter/stem combinations 108' using a variety of anchoring portions and humeral stems portions, including any of those described above.

Figure 6C:
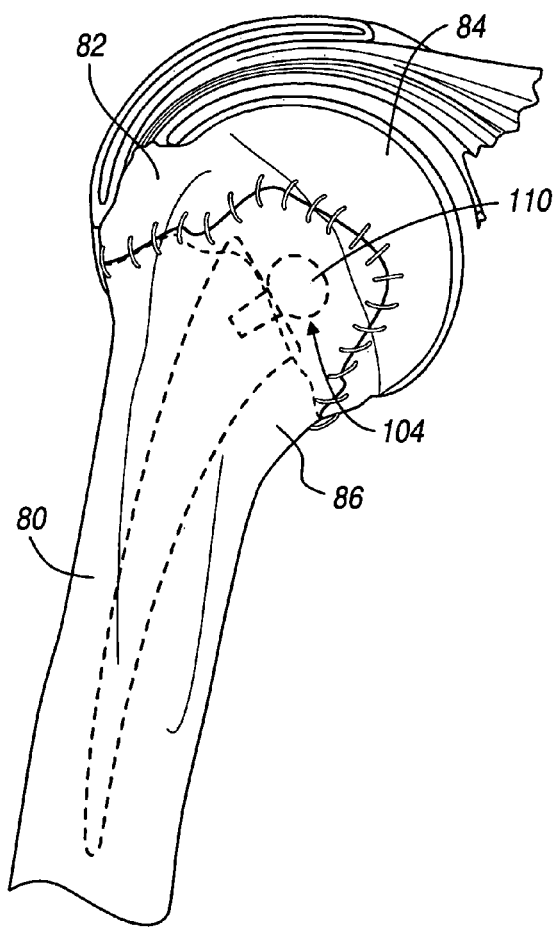

In operation and with reference to FIGS. 6A-6C, the natural humeral head 84, while still attached to the tuberosity 82, is rotated relative to the tuberosity 82 to be examined, exposing the proximal surface 103 of the natural humeral shaft 80 at the proximal end 86. A humeral stem 102 can be selected depending on the condition and size of the natural humeral shaft 80. A longitudinal bore 88 is prepared in the natural humeral shaft 80 to receive the humeral stem 102, as shown in FIG. 6A. Other existing natural shaft fractures can also be repaired, using, if necessary, fixation screws, pins and the like. Depending on the condition of the fracture, the size and robustness of the natural humeral shaft 80 and natural humeral head 84, one of the adapters 104 can be selected from the kit 200 for anchoring into the natural humeral head 84.

When the selected adapter 104 has a bulbous projection 110, the adapter 104 can be first taper-locked with the humeral stem 102, which is then inserted into the longitudinal bore 88, as shown in FIG. 6B, with the bulbous projection 110 exposed above the proximal surface 103 of the natural humeral shaft 80. The natural humeral head 84 can be prepared for receiving the bulbous projection 110 by optionally creating a recess 122 using, for example, an impactor or reamer. The natural humeral head 84 can then be rotated back toward the natural humeral shaft 80 and pressed against the bulbous projection 110 until a snug fit is obtained and the underside surface 120 of the natural humeral head substantially contacts the proximal surface 103 of the natural humeral shaft 82. The natural humeral head is sutured to the humeral shaft 80 and to the tuberosities 82. Alternatively, the adapter 104 can be first anchored into the natural humeral head 84, and then taper-locked into the humeral stem 102.

Figure 6D:
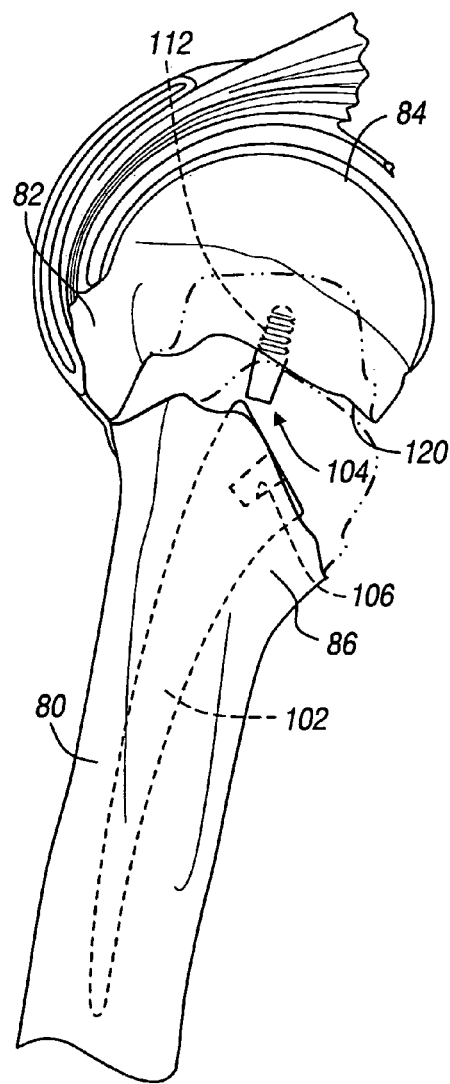
FIG. 6D illustrates an alternative to the procedure of FIG. 6B.

When the selected adapter 104 has an anchoring projection 113 of the threaded screw 112 type, the adapter 104 can be first threaded into the underside surface 120 of the natural humeral head 84, which is then taper-locked with the humeral stem 102, after the humeral stem 102 has been inserted into the longitudinal bore 88, as shown in FIG. 6D. The natural humeral head 84 can be sutured to the humeral shaft 80 and to the tuberosities 82. Other fractures proximal humerus can be repaired and rebuilt, as necessary, using methods known in the art for three-part and four-part fractures of the proximal humerus.

The humeral stem 102 and the adapter 104 can be manufactured from a variety of biocompatible materials such as, for example, Ti6Al4V or CoCrMo. The adapter 104 can also be a hybrid combination of titanium or cobalt chromium with bioabsorbable materials, such as polylactides, plyglycolides, calcium phosphate, hydroxyapatite, etc.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A modular humeral implant for implantation into a humerus that includes a natural humeral shaft and a natural humeral head, the implant comprising:
   a humeral stem for implantation into the natural humeral shaft; and
   an adapter including a first portion and a second portion, the first portion comprising a bulbous projection having a rounded anchoring attachment surface adapted for implantation into an underside of the natural humeral head, the second portion defining a taper lock along a longitudinal axis of the adapter, the bulbous projection extending transversely to the longitudinal axis beyond the taper lock, the taper lock operable for coupling to a proximal end surface of the humeral stem.

2. The humeral implant of claim 1, wherein the taper lock comprises a proximal tapered recess in the humeral stem mating with a tapered projection of the adapter.

3. The implant of claim 2, wherein the bulbous projection is a substantially spherical ball extending beyond the tapered projection of the adapter in a direction transverse to the longitudinal axis.

4. The humeral implant of claim 1, wherein the taper lock comprises a proximal tapered projection in the humeral stem mating with a tapered recess in the adapter.

5. The humeral implant of claim 1, further comprising a plurality of fasteners attaching the natural humeral shaft through the humeral stem to the natural humeral head.

6. The implant of claim 1, wherein the attachment surface includes an attachment device defining outer threads for attachment to the natural humeral head.

7. The implant of claim 1, wherein the attachment surface includes an attachment device having barbs or spikes extending therefrom for attachment to the natural humeral head.

8. The implant of claim 1, wherein the attachment surface includes an attachment device defining outer grooves for attachment to the natural humeral head.

9. The implant of claim 1, wherein the bulbous projection defines an ellipsoid including an attachment device.

10. The implant of claim 1, wherein the bulbous projection is substantially spherical.

11. The humeral implant of claim 1, wherein the bulbous projection includes a plurality of guiding bores receiving elongated anchoring elements anchorable into the natural humeral head.

12. The humeral implant of claim 11, wherein the anchoring elements are attached at one end to a plate at an inferior portion of the bulbous projection.

13. The humeral implant of claim 12, further comprising a fastener operable to push the anchoring elements into the natural humeral head.

14. The humeral implant of claim 13, wherein each anchoring element includes anchoring barbs.

15. The humeral implant of claim 11, wherein the anchoring elements are nitinol wires.

16. A modular humeral implant for implantation into a humerus that includes a natural humeral shaft and a natural humeral head, the implant comprising:
    a humeral stem for implantation into the natural humeral shaft; and
    an adapter including a first portion and a second portion, the first portion comprising a bulbous projection having a rounded anchoring attachment surface adapted for implantation into an underside of the natural humeral head, the second portion comprising an externally threaded extension extending along a longitudinal axis of the adapter, the threaded projection couplable to a proximal end surface of the humeral stem, the bulbous projection extending beyond the threaded extension in a direction transverse to the longitudinal axis.

17. The implant of claim 16, wherein the bulbous projection defines a spherical ball.

18. A kit of modular components for selective implantation into a humerus including a natural humeral shaft and a natural humeral head, the kit comprising:
    a plurality of variably sized humeral stems for selective implantation into the natural humeral shaft; and
    a plurality of adapters for selective use with any one of the plurality of humeral stems, each adapter having a longitudinal axis and a first portion for coupling to a proximal end surface of the humeral stem and a second portion having an attachment device for anchoring into an underside of the natural humeral head, wherein at least one the adapters has a second portion shaped as a spherical ball projection having anchoring spikes and a diameter extending transversely to the longitudinal axis beyond the second portion.

19. The kit of claim 18, wherein the first portion is a male taper received in a female taper of the humeral stem.

20. The kit of claim 18, wherein the first portion is a female taper receiving a male taper of the humeral stem.

21. The kit of claim 18, further comprising variable size fasteners for fastening the natural humeral shaft through the humeral stem to the natural humeral head.

22. A modular humeral implant for implantation into a humerus that includes a natural humeral shaft and a natural humeral head, the implant comprising:
    a humeral stem for implantation into the natural humeral shaft; and
    an adapter including an externally threaded projection along a longitudinal axis, the threaded portion threadably received into a proximal end surface of the humeral stem and a ball-shaped projection connected to the threaded projection, the ball-shaped projection having a porous coating for anchoring and implantation into an underside of the natural humeral head, the ball-shaped projection extending beyond the threaded extension in a direction transverse to the longitudinal axis.

23. A modular humeral implant for implantation into a humerus that includes a natural humeral shaft and a natural humeral head, the implant comprising:
- a humeral stem for implantation into the natural humeral shaft, the humeral stem having a proximal end surface defining a tapered recess; and
- an adapter, the adapter including:
- a tapered projection extending along a longitudinal axis of the adapter, the tapered projection slidably mateable with the tapered recess of the humeral stem, the tapered projection having a first end and a second end, the tapered projection defining an at least partially threaded internal bore;
- a spherical projection attached to the second end of the tapered projection with a plate, the spherical projection defining a plurality of guiding bores extending from the plate through the spherical projection, the spherical projection extending beyond the tapered projection in a direction transverse to the longitudinal axis;
- a plurality of nitinol wires attached to the plate and passing through the guiding bores for anchoring into the natural humeral head; and
- a fastener threadably insertable through the threaded internal bore against the plate.

24. The implant of claim 23, wherein the attachment surface includes a porous coating for attachment to the natural humeral head.

* * * * *

UNITED STATES PATENT AND TRADEMARK OFFICE
CERTIFICATE OF CORRECTION

PATENT NO. : 7,476,253 B1
APPLICATION NO. : 10/916102
DATED : January 13, 2009
INVENTOR(S) : Craig et al.

It is certified that error appears in the above-identified patent and that said Letters Patent is hereby corrected as shown below:

<u>Column 2</u>
Line 61, delete "," after "connect".

<u>Column 3</u>
Line 11, "adaptor" should be --adapter--.

<u>Column 3</u>
Line 51, "tuberority" should be --tuberosity--.

<u>Column 3</u>
Line 57, "adaptor" should be --adapter--.

Signed and Sealed this

Twenty-eighth Day of April, 2009

JOHN DOLL
*Acting Director of the United States Patent and Trademark Office*